United States Patent
Kunert et al.

(10) Patent No.: US 7,625,566 B2
(45) Date of Patent: Dec. 1, 2009

(54) ANTI-IDIOTYPIC MONOCLONAL ANTIBODY REACTIVE WITH HIV NEUTRALIZING ANTIBODY 2F5

(75) Inventors: Renate Kunert, Deutsch-Wagram (AT); Robert Weik, Vienna (AT); Gabriela Stiegler, Fels am Wagram (AT); Hermann Katinger, Vienna (AT)

(73) Assignee: Polymun Scientific Immunbiologische Forschung GmbH, Vienna (AU)

( * ) Notice: Subject to any disclaimer, the term of this patent is extended or adjusted under 35 U.S.C. 154(b) by 866 days.

(21) Appl. No.: 10/501,726

(22) PCT Filed: Jan. 17, 2003

(86) PCT No.: PCT/EP03/00455

§ 371 (c)(1), (2), (4) Date: Jul. 16, 2007

(87) PCT Pub. No.: WO03/059953

PCT Pub. Date: Jul. 24, 2003

(65) Prior Publication Data

US 2005/0080240 A1     Apr. 14, 2005

(30) Foreign Application Priority Data

Jan. 17, 2002   (EP)   ................... 02001250

(51) Int. Cl.
*A61K 39/42* (2006.01)
*C12N 5/06* (2006.01)
*C12P 21/08* (2006.01)

(52) U.S. Cl. .............. 424/184.1; 435/339.1; 530/388.35

(58) Field of Classification Search ........................ None
See application file for complete search history.

(56) References Cited

FOREIGN PATENT DOCUMENTS

| EP | 0 503 916 A1 | * | 3/1991 |
| EP | 0 498 767 A2 | | 8/1992 |
| EP | 0 503 916 A1 | | 9/1992 |
| EP | 0 570 357 A2 | | 11/1993 |
| WO | WO 94/08601 A1 | | 4/1994 |
| WO | WO 97/16204 A1 | | 5/1997 |
| WO | WO 97/34636 A | | 9/1997 |
| WO | WO 98/17799 A1 | | 4/1998 |

OTHER PUBLICATIONS

Muster, T., et al., 1993, A conserved neutralizing eptiope on gp41 of human immunodeficiency virus type 1, J. Virol. 67(11):6642-6647.*
Walker, B. D., and D. R. Burton, 2008, Toward an AIDS vaccine, Science 320:760-764.*
Trkola, A., et al., 2005, Delay of HIV-1 rebound after cessation of antiretroviral therapy through passive transfer of human neutralizing antibodies, Nat. Med. 11(6):615-622.*
Haynes, B. F., et al., 2005, Cardiolipin polyspecific autoreactivity in two broadly neutralizing HIV-1 antibodies, Science 308:1906-1909.*
Montefiori, D. C., 2005, Neutralizing antibodies take a swipe at HIV in vivo, Nat. Med. 11(6):593-594.*
Moore, J. P., and D. R. Burton, 1999, HIV-1 neutralizing antibodies: How full is the bottle? Nat. Med. 5(2):142-144.*
Gallo, R. C., 2005, The end of the beginning of the drive to an HIV-preventive vaccine: a view from over 20 years, The Lancet 366:1894-1898.*

* cited by examiner

*Primary Examiner*—Jeffrey S. Parkin
(74) *Attorney, Agent, or Firm*—Rothwell, Figg, Ernst & Manbeck, P.C.

(57) ABSTRACT

The invention relates to Ab2-type anti-idiotypic antibodies and fragments thereof which mimic HVI-1 epitopes that are otherwise cryptic to the immune system and which antibodies or fragments thereof are directed against potently neutralizing anti-HIV-1 antibodies. The invention further relates to a hybridoma cell line 3H6 expressing the anti-idiotypic antibody and to pharmaceutical compositions containing the antibody or fragment thereof. The invention also relates to HIV-1 neutralizing Ab3-type antibodies elicited upon administration of the Ab2-type anti-idiotypic antibody or fragment thereof and to pharmaceutical compositions containing them. The invention also relates to the use of the present antibodies or fragments thereof as screening tools or as diagnostic or therapeutic agents.

9 Claims, 3 Drawing Sheets

FIG. 6

SEQUENCE LISTING

```
<160> NUMBER OF SEQ ID NOS: 15

<210> SEQ ID NO 1
<211> LENGTH: 6
<212> TYPE: PRT
<213> ORGANISM: Human immunodeficiency virus type 1
<220> FEATURE:
<221> NAME/KEY: DOMAIN
```

```
<222> LOCATION: (1)..(6)
<223> OTHER INFORMATION: highly conserved sequence located on gp41 of
      HIV-1

<400> SEQUENCE: 1

Glu Leu Asp Lys Trp Ala
1               5

<210> SEQ ID NO 2
<211> LENGTH: 6
<212> TYPE: PRT
<213> ORGANISM: Human immunodeficiency virus type 1
<220> FEATURE:
<221> NAME/KEY: DOMAIN
<222> LOCATION: (1)..(6)
<223> OTHER INFORMATION: highly conserved sequence located on gp41 of
      HIV-1

<400> SEQUENCE: 2

Glu Leu Asp Asn Trp Ala
1               5

<210> SEQ ID NO 3
<211> LENGTH: 6
<212> TYPE: PRT
<213> ORGANISM: Human immunodeficiency virus type 1
<220> FEATURE:
<221> NAME/KEY: DOMAIN
<222> LOCATION: (1)..(6)
<223> OTHER INFORMATION: highly conserved sequence located on gp41 of
      HIV-1

<400> SEQUENCE: 3

Glu Leu Asn Lys Trp Ala
1               5

<210> SEQ ID NO 4
<211> LENGTH: 7
<212> TYPE: PRT
<213> ORGANISM: Human immunodeficiency virus type 1
<220> FEATURE:
<221> NAME/KEY: DOMAIN
<222> LOCATION: (1)..(7)
<223> OTHER INFORMATION: highly conserved sequence located on gp41 of
      HIV-1

<400> SEQUENCE: 4

Leu Glu Leu Asp Lys Trp Ala
1               5

<210> SEQ ID NO 5
<211> LENGTH: 7
<212> TYPE: PRT
<213> ORGANISM: Human immunodeficiency virus type 1
<220> FEATURE:
<221> NAME/KEY: DOMAIN
<222> LOCATION: (1)..(7)
<223> OTHER INFORMATION: highly conserved sequence located on gp41 of
      HIV-1

<400> SEQUENCE: 5

Leu Glu Leu Asp Asn Trp Ala
1               5

<210> SEQ ID NO 6
<211> LENGTH: 7
<212> TYPE: PRT
<213> ORGANISM: Human immunodeficiency virus type 1
<220> FEATURE:
```

```
<221> NAME/KEY: DOMAIN
<222> LOCATION: (1)..(7)
<223> OTHER INFORMATION: highly conserved sequence located on gp41 of
      HIV-1

<400> SEQUENCE: 6

Leu Glu Leu Asn Lys Trp Ala
1               5

<210> SEQ ID NO 7
<211> LENGTH: 7
<212> TYPE: PRT
<213> ORGANISM: Human immunodeficiency virus type 1
<220> FEATURE:
<221> NAME/KEY: DOMAIN
<222> LOCATION: (1)..(7)
<223> OTHER INFORMATION: highly conserved sequence located on gp41 of
      HIV-1

<400> SEQUENCE: 7

Glu Leu Asp Lys Trp Ala Ser
1               5

<210> SEQ ID NO 8
<211> LENGTH: 7
<212> TYPE: PRT
<213> ORGANISM: Human immunodeficiency virus type 1
<220> FEATURE:
<221> NAME/KEY: DOMAIN
<222> LOCATION: (1)..(7)
<223> OTHER INFORMATION: highly conserved sequence located on gp41 of
      HIV-1

<400> SEQUENCE: 8

Glu Leu Asp Asn Trp Ala Ser
1               5

<210> SEQ ID NO 9
<211> LENGTH: 7
<212> TYPE: PRT
<213> ORGANISM: Human immunodeficiency virus type 1
<220> FEATURE:
<221> NAME/KEY: DOMAIN
<222> LOCATION: (1)..(7)
<223> OTHER INFORMATION: highly conserved sequence located on gp41 of
      HIV-1

<400> SEQUENCE: 9

Glu Leu Asn Lys Trp Ala Ser
1               5

<210> SEQ ID NO 10
<211> LENGTH: 8
<212> TYPE: PRT
<213> ORGANISM: Human immunodeficiency virus type 1
<220> FEATURE:
<221> NAME/KEY: DOMAIN
<222> LOCATION: (1)..(8)
<223> OTHER INFORMATION: highly conserved sequence located on gp41 of
      HIV-1

<400> SEQUENCE: 10

Leu Glu Leu Asp Lys Trp Ala Ser
1               5

<210> SEQ ID NO 11
<211> LENGTH: 8
<212> TYPE: PRT
<213> ORGANISM: Human immunodeficiency virus type 1
```

```
<220> FEATURE:
<221> NAME/KEY: DOMAIN
<222> LOCATION: (1)..(8)
<223> OTHER INFORMATION: highly conserved sequence located on gp41 of
      HIV-1

<400> SEQUENCE: 11

Leu Glu Leu Asp Asn Trp Ala Ser
1               5

<210> SEQ ID NO 12
<211> LENGTH: 8
<212> TYPE: PRT
<213> ORGANISM: Human immunodeficiency virus type 1
<220> FEATURE:
<221> NAME/KEY: DOMAIN
<222> LOCATION: (1)..(8)
<223> OTHER INFORMATION: highly conserved sequence located on gp41 of
      HIV-1

<400> SEQUENCE: 12

Leu Glu Leu Asn Lys Trp Ala Ser
1               5

<210> SEQ ID NO 13
<211> LENGTH: 12
<212> TYPE: PRT
<213> ORGANISM: Artificial sequence
<220> FEATURE:
<223> OTHER INFORMATION: homologous to HIV-1
<220> FEATURE:
<221> NAME/KEY: DOMAIN
<222> LOCATION: (4)..(12)
<223> OTHER INFORMATION: highly conserved sequence located on gp41 of
      HIV-1

<400> SEQUENCE: 13

Gly Gly Gly Leu Glu Leu Asp Lys Trp Ala Ser Leu
1               5                   10

<210> SEQ ID NO 14
<211> LENGTH: 122
<212> TYPE: PRT
<213> ORGANISM: Artifical sequence
<220> FEATURE:
<223> OTHER INFORMATION: Antibody 3H6 (ECACC Acc.No. 01100279)
<220> FEATURE:
<221> NAME/KEY: CHAIN
<222> LOCATION: (1)..(122)
<223> OTHER INFORMATION: heavy chain variable region (vH) of
      anti-idiotypic antibody 3H6

<400> SEQUENCE: 14

Gly Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Thr Asp Tyr
            20                  25                  30

Phe Met His Trp Val Lys Gln Ser His Gly Lys Ser Leu Asp Trp Ile
        35                  40                  45

Gly Tyr Ile Asn Cys Tyr Thr Gly Ala Thr Asn Tyr Ser Gln Lys Phe
    50                  55                  60

Lys Gly Lys Ala Thr Phe Thr Val Asp Thr Ser Ser Asn Thr Ala Tyr
65                  70                  75                  80

Met Gln Phe Asn Ser Leu Thr Ser Glu Asp Ser Ala Val Tyr Tyr Cys
                85                  90                  95

Ala Arg Thr Ser Ile Gly Tyr Gly Ser Ser Pro Pro Phe Pro Tyr Trp
```

```
                  100              105              110
Gly Gln Gly Thr Leu Val Thr Val Ser Ala
        115                  120

<210> SEQ ID NO 15
<211> LENGTH: 107
<212> TYPE: PRT
<213> ORGANISM: Artifical sequence
<220> FEATURE:
<223> OTHER INFORMATION: Antibody 3H6 (ECACC Acc.No. 01100279)
<220> FEATURE:
<221> NAME/KEY: CHAIN
<222> LOCATION: (1)..(107)
<223> OTHER INFORMATION: light chain variable region (vL) of
      anti-idiotypic antibody 3H6

<400> SEQUENCE: 15

Glu Thr Thr Val Thr Gln Ser Pro Ala Ser Leu Ser Met Ser Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Arg Leu Leu Ile
        35                  40                  45

Ser Asp Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Asn Leu Glu Ile Lys
            100                 105
```

ANTI-IDIOTYPIC MONOCLONAL ANTIBODY REACTIVE WITH HIV NEUTRALIZING ANTIBODY 2F5

CROSS-REFERENCE TO RELATED APPLICATION

This application is a National Phase of International Application No. PCT/EP03/00455, filed Jan. 17, 2003.

TECHNICAL FIELD

The present invention is in the fields of immunology and vaccine development and relates to antibodies that mimic an epitope on gp41 of HIV-1. The invention further relates to applications of the antibodies and fragments thereof, including their use for eliciting HIV-1 neutralizing antibodies in mammalian hosts and to HIV-1 neutralizing antibodies elicited by said anibodies or antibody fragments. The invention also relates to pharmaceutical compositions, in particular vaccines, containing such antibodies or antibody fragments for either active or passive immunization to inhibit or prevent HIV-1 infection in mammalian individuals.

BACKGROUND OF THE INVENTION

Anti-idiotypic antibodies (Ab2) are directed against the antigen binding site of other antibodies (Ab1). Epitopes of diverse pathogenic antigens may be mimicked functionally and structurally by those Ab2s. Thus, Ab2s are able to induce anti-anti-idiotypic antibodies (Ab3) that are Ab1-like and have similar biological properties [1].

Different kinds of Ab2s are distinguished after immunization with Ab1 [2, 3]. The Ab2α (Ab2-alpha) recognizes idiotypes at the distal position from Ab1 paratope and does not interfere with Ab1 binding to the nominal epitope. Ab2s beta (Ab2β) are directed to the paratope of Ab1s and bear the internal image of the antigen. Ab2β can compete with the nominal antigen for binding to the idiotype and to antigen-specific xenogeneic antibodies. A third category, termed Ab2γ (Ab2-gamma) recognizes idiotopes physically close to the binding site but does not behave as a surrogate antigen [4].

Moreover, internal image anti-idiotype antibodies may exhibit identical three-dimensional conformation or amino-acid sequence homology with the epitope. This has been shown for the reovirus system, where the amino acid sequence of the idiotype had the same motif as the virus hemagglutinin [5]. Thus the virus-receptor binding on susceptible cells can be prevented.

Generally, the advantages of anti-idiotypic antibodies over other vaccines applying peptide antigens or inactivated viruses can be manifold [6]. They do not involve any viral components, they are safe but do not miss any specificity by their mimicry of single epitopes. They can be produced easily in large quantities for immunization. Ab2s can even induce an immune response against single neutralizing epitopes that may not be immunogenic on the native antigen. They thus can break immunogenic unresponsiveness to certain antigens as has been demonstrated in neonatal mice [7]. Active immunotherapy with Ab2-based vaccines have proven very potent to induce antigen-specific Ab3 in cancer patients against tumor cells [8-11].

Ab2s that display internal images of antigen (Ab2β) have also induced protective immunity against infective pathogens [12].

HIV-1 infections may be accessible to Ab2 therapy because of the importance of neutralizing antibodies in the control of HIV-1 infections [13]. The possibility to induce neutralizing Ab3 in various systems including HIV-1 has been described [14].

Cross-reactivity of HIV-1 antigens with various normal human antigens suggests a potential advantage of single epitope Ab2 vaccines over multiple epitope vaccines [15]. Different approaches for the induction of a neutralizing humoral immune response have been made with anti-idiotypic antibodies. The most promising experiments were undertaken with anti-CD4 specific mAbs, which are able to induce HIV-1 neutralizing antibodies in vitro [16, 17]. The anti-CD4 mAbs Leu3a and IOT4A were also tested in clinical studies [18, 19] and were-shown to induce a gp120 cross-reacting immune response that inhibits gp120 binding to CD4. Ab2s against V3 loop peptides were also generated and used in different in vitro studies [20-22]. In different animal models they induced Ab3s with the ability of binding the autologous peptides as well as gp120, but could not neutralize HIV-1 in an in vitro experiment. Only one Ab2 has been described having the potential as a vaccine against HIV-1 [23].

In principle, Ab2 beta antibodies raised against antibodies neutralizing HIV-1 might have an enormous potential for vaccine design. A vaccine against HIV-1 must induce both, cellular as well as humoral immune responses. HIV-1 specific CTL-responses can be induced by various experimental vaccines such as DNA-vaccines [24] or chimeric influenza live viruses administered as nasal spray and expressing HIV-1 epitopes [25]. Reasonable experimental vaccines inducing neutralizing antibody responses are so far generally not available. The human monoclonal antibody 2F5 (produced by hybridoma cell line ECACC Accession No. 90091704) broadly and potently neutralizes primary HIV-1 isolates [26]. Thus, mAb 2F5 is an extraordinary interesting tool for the design of an anti-HIV-1 vaccine leading to properly induced humoral immune responses. It recognizes the highly conserved six amino acid core epitope sequence ELDKWA (SEQ ID NO:1) on the virus envelope ectodomain gp41 [27]. 2F5-like specific antibodies are only rarely found in sera of HIV-1 infected individuals. HIVIG (pooled sera of more than 70 HIV-1 positive donators) do not show significant 2F5-like specific binding to gp160 and/or gp41. The region on gp41 to which 2F5 binds is obviously cryptic to the human immune system during natural infection. Different mechanisms might contribute to its immuno-cryptic behavior. One explanation might be that the human complement factor H which is abundantly present in normal human serum has a binding domain in that region of gp41 thus masking it against immune recognition [28]. This mAb, although being a broad and potent entry blocker (neutralizers) of HIV-1 binds only very weakly to free virus and HIV-1 infected cells. [30]. It is therefore concluded that this fusogenic region on gp41 is only exposed during the event of fusion of the HIV-1 with the host cell. That might on the one hand give an additional explanation for the cryptic nature of these neutralizing epitopes during natural infection. On the other hand HIV-1 isolates that are neutralization insensitive to this antibody have not been found so far.

In earlier studies the core epitope motif ELDKWA (SEQ. ID NO: 1) of 2F5 was integrated into different antigenic formats. The presentation of the ELDKWA-motif (SEQ ID NO: 1) on the haemagglutinin of influenza life virus was able to induce long lasting mucosal immune responses detected as 2F5-like specific IgA's in mouse faeces upon repeated immunization as a mucosal nasal spray [25]. However, quantities of IgA sufficient to prove in vitro neutralization potency could not be extracted from the faeces samples. Other forms of presenting the 2F5-core epitope for immunization such as fusion to the hepatitis B surface antigen expressed in yeast induced very high 2F5-like specific ELISA-titers in immunized BALB/c mice. However, the sera of those animals did not show any significant in vitro neutralization potency [36]. Peptide versions of the 2F5 epitope were also poorly immunogenic.

BRIEF DESCRIPTION OF THE DRAWINGS

FIG. 1 shows the reduction of binding capacity of 2F5 to the precoated epitope after preincubation of 2F5 with Ab2 3H6. Serial dilutions of 2F5 starting with 100 ng/mL were preincubated with 50 ng/mL or 500 ng/mL 3H6 or with the unspecific Ab2 6H8. After 1 hour the dilutions were allowed to react with GGGLELDKWASL (SEQ ID NO:13) at the microtiter plate and 2F5 was detected.

FIG. 2 shows a neutralization assay of 10 μg/mL 2F5 and 2G12 with increasing amounts of 3H6 and irrelevant mouse IgG.

FIG. 3 shows the binding of ascites and serum samples of 3H6 immunized mice to gp160.

FIG. 4 shows the binding of ascites and serum samples of 3H6 immunized mice to GGGLELDKWASL (SEQ ID NO.13).

FIG. 5 shows the result of a competition assay of 3H6 immunized mice sera with 2F5 in an ELISA binding study to precoated GGGLELDKWASL (SEQ ID NO:13).

FIG. 6 is a schematic delineation of the fusion protein mo/hu3H6/IL-15.

DESCRIPTION OF THE INVENTION

It is an object of the invention to generate antigen binding components which are capable to induce neutralizing humoral immune responses against HIV-1. A further object of the invention is to provide novel antibodies or antibody fragments which are able to induce HIV-1 neutralizing antibodies.

The invention discloses murine antibodies and fragments thereof which are directed against an antibody of the gp41 antigen on HIV-1. In particular, the invention describes the generation of anti-idiotype murine Ab2β directed against the human monoclonal antibody 2F5 which is known to react with a cryptic neutralizing epitope on gp41 of HIV-1. One of the Ab2's of the present invention, i.e. the murine monoclonal Ab2 designated 3H6 (deposited under the provisions of the Budapest Treaty on the Deposit of Microorganisms at PHLS Porton Down, Salisbury, UK; ECACC Acc. No. 01100279) blocks the binding of the human Ab1 2F5 to a synthetic epitope containing at least the core epitope sequence ELDKWA (SEQ ID NO:1) as well as to gp160. 3H6 is also able to diminish the HIV-1 neutralizing potency of 2F5.

The present invention also relates to Fab-fragments derived from 3H6 antibodies, which were shown to induce neutralizing immune responses in the sera of human and non-human mammals applying a simple prime/boost regimen of immunization. Thus, 3H6 Fab-fragments successfully mimick an epitope that apparently lacks immunogenicity or is only poorly immunogenic on the native HIV-1 during natural infection.

An "antibody fragment" in the context of the present invention is an antigen-binding part of the whole antibody which retains the binding specificity of the whole antibody molecule. The term encompasses, for example, Fab-, F(ab')2-, Fv- and scFv-fragments. Antibody fragments can be obtained by conventional techniques well known in the art such as proteolytic digestion of antibodies, for example by papain digest, or through genetic engineering.

The antibodies and antibody fragments of the present invention can also be prepared by synthetic methods known in the art, such as peptide synthesis or recombinant DNA technology, once the structural nature of the antibody fragments has been analyzed by crystallization studies, sequencing methods and/or other methods well known in the art.

In another embodiment, the invention relates to "humanized" antibodies and antibody fragments. "Humanized" means that a non-human antibody or antibody fragment is linked with part of a human antibody. Usually it means that the complimentarity determining regions (CDR) from the variable regions of a non-human, e.g. rodent, antibody are combined with framework regions from the variable regions of a human antibody, e.g. from a human IgG. In doing so the fragment containing the antigen binding site of the non-human antibody is inserted into a suitable human antibody. Methods for "humanizing" antibodies are state of the art. For instance, an exon encoding the variable region containing the CDR of the non-human antibody may be spliced into the framework sequence of a suitable human antibody. Further, a Fab-fragment of the non-human antibody may be coupled with a suitable Fc-fragment of a suitable human antibody. Suitable human frameworks may be found by homology searches in databases on the basis of homology to the non-human antibody.

"Humanized" antibody fragments according to the present invention may also be derived from synthetic phage libraries which use randomized combinations of synthetic human antibody variable regions, by selecting on 2F5 antibodies as antigen. Humanized antibodies are referred to hereinafter by using the prefix "hu", e.g. the term "hu3H6" refers to a humanized 3H6 antibody.

In a still further embodiment the invention relates to chimeric antibodies. "Chimeric" antibodies are antibodies in which the whole of the variable regions of a non-human, in particular rodent, antibody are expressed along with human constant regions of antibodies. This may provide antibodies with human effector functions. "Chimeric" antibodies may be created on the molecular level by fusing non-human exons encoding variable regions containing the antigen binding site with human exons encoding antibody constant regions. Chimeric mouse/human antibodies are identified hereinafter by the prefix "mo/hu", e.g. the term "mo/hu3H6" refers to a chimeric mouse/human 2H6 antibody.

Where the term "3H6" is used without identifying prefix the term shall relate to the murine Ab2 antibody 3H6, e.g. as produced by cell line 3H6 (ECACC Acc. No. 01100279), unless another meaning is derivable from the respective context. Such other meaning would include using the term 3H6 as a generic term encompassing each one or all of the group elements: murine, chimeric and humanized 3H6 antibodies.

In yet another embodiment the present invention relates to an antibody-cytokine construct, wherein the vH and vL chains of a chimeric mo/hu3H6 antibody (FIG. 6) are fused with human Fc and ckappa chains, resulting in a recombinant expression protein having an IgG isotype. A chimeric IgG molecule is able to pass the placenta, wherefore it is expected that the aforementioned construct may sucessfully interfere with and inhibit or prevent a mother-to-child transmission of HIV-1.

Anti-idiotypic antibody 3H6 Fab-fragments as well as the mo/hu3H6 Fc-gamma antibodies induce humoral immune responses and trigger the immune system to induce neutralising antibodies.

In a further embodiment the present invention relates to an antibody or antibody fragment that is associated, e.g. fused or coupled, with an immunoactive molecule that improves the immunogenic nature of the antibodies induced by the antibody or antibody fragment upon administration to a mammalian individual. For instance, the antibody fragment may be coupled to a structure, for instance a cytokine such as, e.g., IL-4, which enhances the immunoreactivity of said mammal and preferably causes an increased B-cell response, which is of particular importance in the treatment of HIV. The present invention also relates to entire Ab2 antibodies, particularly to antibody 3H6 including murine 3H6, chimeric mo/hu3H6 and hu3H6, wherein the antibody is associated (e.g. coupled, fused or linked) with any such immunoresponse stimulating molecule, as well as to mixtures comprising at least one antibody and/or anti-HIV-effective fragment thereof in combination with at least one cytokine-associated, particularly IL-4 associated, antibody and/or anti-HIV-effective fragment thereof. The term "anti-HIV-effective fragment" as used herein relates to antibody fragments that are reactive with HIV-1 neutralizing antibody 2F5 (ECACC Accession No. 90091704) and which inhibit or prevent the HIV-1 neutralization activity of antibody 2F5 and/or the binding of antibody 2F5 to gp41 of HIV-1, and which are preferably effective in eliciting, upon proper administration to a mammal, 2F5 type anti-HIV-1 antibodies.

Therapeutic use of interleukins in the treatment of cancer and viral infections is applied since years. Additionally, some cytokines like IL-2 are diminished in early phases of infection. Especially in HIV-1 therapies considerable indications and independent studies point out that IL-15 may be of great benefit.

Similarly to IL-2, IL-15 is responsible for the proliferation of activated T- and NK-cells, assists the distribution of IFN-γ and stimulates the generation of immune-globulines in B-cells. IL-15 mRNA is detected in different tissues and is regulated tightly. IL-15 induces proliferation of $CD8^+$ memory cells, while IL-2 inhibits the proliferation of $CD8^+$ memory cells. Therefore, IL-15 was chosen as a possible candidate in the concept of developing an improved HIV vaccine according to the present invention, and particularly at least for the reasons that it a) supports the generation of neutralising antibodies in a patient's B lymphocytes, and b) also stimulates the cellular immunity by increasing the number of $CD8^+$ memory cells of said patient. Moreover, while infusion of IL-2 to AIDS patients showed severe side effects at higher doses, IL-15 is far less harmful and is even detected in new-born babies.

Accordingly, in a further embodiment the present invention relates to an anti-idiotypic Ab2 antibody or antibody fragment reactive with antibody 2F5, preferably to Ab2 3H6 or a fragment thereof, that is associated, e.g. fused or coupled, with IL-15 as an immunoactive molecule. In a preferred embodiment, the invention relates to a fusion protein consisting of the chimeric mo/hu3H6 or humanized antibody hu3H6 and human IL-15, i.e. to a recombinant protein which is a fusion protein consisting of mo/hu3h6 or hu3H6 and a human IL-15 tail at the C-terminus of the antibody heavy chain (FIG. 6). The fusion proteins induce neutralising, 2F5 like antibodies in a mammalian recipient while at the same time proliferation of $CD8^+$ memory cells is stimulated through the action of the IL-15 tail.

Moreover, apart from the aforementioned activity of the cytokine-associated Ab2 antibodies of the present invention to induce memory T cell activity, a combination of an Ab2 antibody or anti-HIV-effective fragment thereof and a cytokine-associated Ab2 antibody or anti-HIV-effective fragment thereof allows to develop optimal therapeutic effects by adjusting the ratio of the components to each other, typically in an anti-HIV-1 vaccine. In a preferred embodiment, the invention relates to a mixture or composition, typically an HIV-1 vaccine, comprising at least one antibody or effective fragment thereof selected from the group consisting of 3H6, fragment of 3H6, mo/hu3H6, fragment of mo/hu3H6, hu3H6, and fragment of hu3H6 in combination with at least one cytokine-associated, preferably IL-4 or IL-15 associated antibody or effective fragment thereof, the antibody or fragment being selected from the same group consisting of 3H6, fragment of 3H6, mo/hu3H6, fragment of mo/hu3H6, hu3H6, and fragment of hu3H6.

The proper ratio can be determined using in vitro models for each recipient prior to administration. Usally this determination will comprise decreasing the Ab2-associated IL-15 concentration to a minimal level and to supplement the hu3H6 antibody up to a concentration that ensures at least some, preferably the best possible induction of the humoral immune response.

Sera of 3H6 induced immune responses show both specific binding inhibition patterns of 2F5 on the antigen as well as significant in vitro neutralization potency. Furthermore, the anti-2F5-Ab2β 3H6, while reacting strongly with the homologous Ab1, does not recognize isotype matched control antibodies demonstrating high specificity for the idiotype with no cross-reactivity to irrelevant Ig's.

Thus, the anti-idiotypic antibody 3H6 may be used, either directly as a vaccine to induce protective and neutralizing immune responses, or as a tool contributing to the design of an HIV-1 vaccine that also successfully induces protective and neutralizing B-cell responses. Ab2s can be suitable for vaccination of HIV-1 infected newborns, whose immune system might be tolerant to stimulation with other antigens [37, 38].

At the first glance Ab2 3H6 represents a vaccine antigen capable to induce neutralizing immune responses. Immunization with Ab2 3H6 shall avoid the induction of antibody-dependent enhancement of infection responses (ADE) observed in polyclonal sera of HIV-1 positive individuals [39-42]. The Ab1 2F5 was passively administered in gram-quantities to human volunteers. No signs of ADE have been observed in these human volunteers despite the fact that complement activation was detected [29]. As Ab2 3H6 induces 2F5-like specificities in the sera of immunized animals it can be expected that ADE-phenomena observed with polyclonal sera of HIV-positive individuals [43] can be avoided upon vaccination with Ab2 3H6.

For the use as a pharmaceutical the antibodies and antibody fragments of the present invention may be part of a composition together with a pharmaceutically acceptable carrier. Thus, in a further embodiment the present invention relates to pharmaceutical compositions, particularly vaccines, which comprise the Ab2 antibodies or antibody fragments of the present invention together with a suitable, optionally immunogenic, carrier and/or adjuvant.

In yet another embodiment the present invention relates to Ab3 antibodies (anti-anti-idiotypic antibodies) elicted by the present Ab2 antibodies or antibody fragments of the 3H6 type, as well as to pharmaceutical compositions, including vaccines, which comprise Ab3 antibodies or antibody fragments directed against Ab2 3H6 and preferably directed against the binding epitope of Ab2 3H6. In a most preferred embodiment, these Ab3 ntibodies or antibody fragments are of a nature such that they neutralize HIV-1. Pharmaceutical compositions containing such an Ab3 antibody or fragment thereof are useful for passive immunization against HIV-1.

The antibodies or antibody fragments of the present invention may be administered in dosages of about 0.5 to about 10 μg/kg body weight, and preferably boosted in one or more, usually periodic, intervals. The pharmaceutical compositions of the present invention containing either Ab2 3H6 antibodies or fragments thereof, or anti-3H6 Ab3 antibodies or fragments whereof may be administered prophylactically to prevent an individual from getting HIV-1 infected, as well as therapeutically to inhibit or stop progression of disease in an HIV-1 infected individual.

EXAMPLE 1

Generation of 3H6 Antibodies

Animals:

Female BALB/c mice, 8-10 weeks old, were obtained from Charles River (Sulzfeld, Germany).

Antibodies:

Immunoglobulin subclass standards and isotype-specific anti-mouse antisera were purchased from Sigma (St. Louis, Mass.). Monoclonal anti-HIV-1 antibody 2F5 was purified and used as antigen binding fragment (Fab') for immunization. Antibodies were digested with Mercuripapain (Sigma) and the digest purified with Protein-A-Sepharose 4 FF-column.

Immunization of Animals:

50 μg of the 2F5 Fab' were injected intraperetoneal once in complete Freund's adjuvant (CFA) and after three and six weeks again with incomplete Freund's adjuvant (IFA). Four days before spleen-ectomization the animals were boosted for the last time. Spleenocytes were prepared on day 46 after the first immunization.

Generation of Hybridoma Secreting Mouse IgG:

The serum titer of mice was used as criteria for the development of immunocompetent spleenocytes. Only mice with an anti-2F5 titer of at least 1:100,000 were used for fusion. According to standard protocols the spleen cells were fused with X63-Ag-8.653 cells and plated in 96-well plates. HAT-selection was started the day after fusion and supernatants of growing wells were first tested for mouse IgG production using a mouse mAb as standard protein. Polyclonal goat anti-mouse-γ-chain antibody (Sigma) was diluted 1:500 in coating buffer (0.1N $Na_2CO_3/NaHCO_3$ pH 9.6) and 100 μL per well were precoated onto microtiter plates (ELISA grade I; Nunc, Denmark). After each incubation step the plates were washed three times with PBS containing 0.1% Tween 20 adjusted to pH 7.2. The standard mouse mAb was serially diluted, starting with 200 ng/mL (dilution buffer contained 1% BSA in washing buffer). 50 μL per well of standard or serially diluted sample were allowed to bind to the precoated well for 1 h, and after washing the plates, we used 50 μL of 1:5,000 diluted goat anti-mouse IgG+IgM poly HRP80 (RDI Inc.) as second antibody. After 1 h incubation time, the plates were stained with OPD and read at 492 nm (reference wavelength 620 nm).

For the screening of antibodies against the 2F5 idiotype, the supernatants of 2170 HAT-resistant Hybridoma were tested for IgG production. 65 positive clones were found. Approx. 10% of supernatants of the IgG positive clones were also reacting with antibody 2F5.

EXAMPLE 2

Identification of Neutralizing Antibodies

Idiotype Binding Assay:

For initial screening of idiotype binding antibodies, 96-well microtiter plates were coated overnight at 4° C. with 2F5-IgG1, 2F5-IgG3 or 2G12, another gp120 recognizing human anti-HIV-1 antibody [31]. Samples were diluted $2^8$ in dilution buffer starting with 200 ng/mL. The Ab2s were visualized as described for the mouse IgG ELISA.

The antibodies 3H6, 4F6, and 6F8 could be stabilized and were tested for their binding capacity in ELISA with different precoatings. The anti-idiotypic antibody 1G1, directed against a different neutralizing anti-HIV-1 antibody, namely 2G12 (ECACC Acc. No. 93091517; for details see WO 96/33219), served as control. Table 1 shows the relative binding properties of Ab2s with different idiotypes. 4F6 and 6F8 reacted with all antibodies and seemed to recognize an epitope at the constant region. The antibody 1G1 specifically binds to 2G12, while 3H6 recognizes both isotypes of 2F5 and it was negative for 2G12.

TABLE 1

| Ab2 | 2F5 IgG1 | 2F5 IgG3 | 2G12 IgG1 |
|---|---|---|---|
| 4F6 | +++ | ++ | ++++ |
| 6F8 | ++ | ++++ | ++ |
| 3H6 | ++++ | +++ | − |
| 1G1 | − | − | +++ |

Idiotype Inhibition Assay of Ab2 3H6:

Competitive binding assays were performed as previously described [32]. Different concentrations of Ab2 (50, 500 ng/mL) were preincubated with 1:2 dilutions of 2F5 starting with 100 ng/mL. After 1 hour the antibodies were allowed to react with the antigen on the plate. The solid phase was coated with the synthetic 2F5 epitope GGGLELDKWASL (SEQ. ID NO.13) at a concentration of 2 μg/mL and the final binding of 2F5 was detected as described [33].

Figure 1:
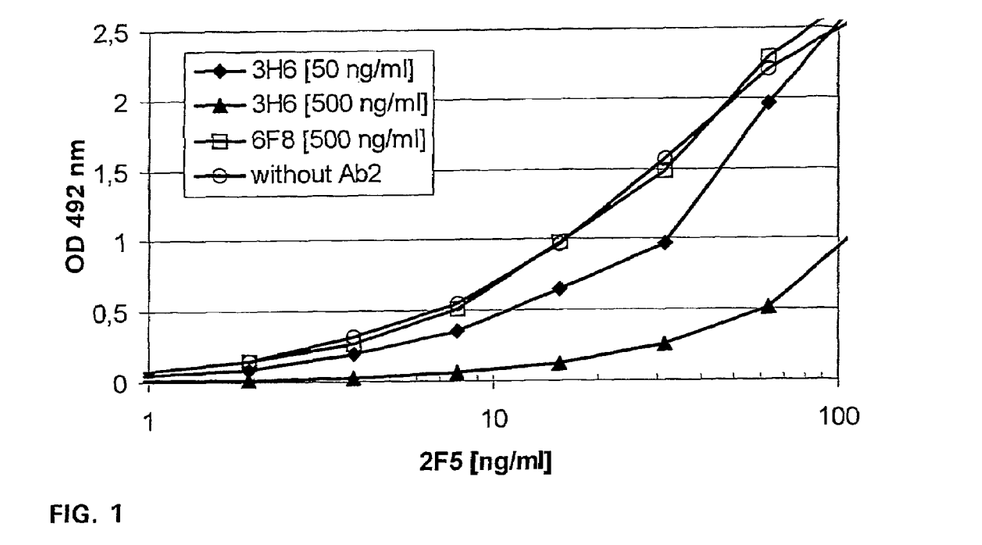

The ELISA competition assay was designated to describe the remaining binding capacity of 2F5 to the ELDKWA-epitope (SEQ ID NO: 1) after preincubation with Ab2. Ab2 3H6 inhibits or prevents the binding of 2F5 to the epitope depending on the concentrations applied. FIG. 1 describes the decline of 2F5 binding to the GGGLELDKWASL (SEQ ID NO. 13) precoated plate with increasing concentrations of 3H6. Even 50 ng/mL 3H6 could reduce the binding properties of 31 ng/mL 2F5 by more than one third (37% reduction of the OD) and 500 ng/mL resulted in 83% reduction of OD while the Ab2 6F8 did not diminish the binding of 2F5 to the epitope. Since the binding affinity of 2F5 to the GST- (glutathion S-transferase) ELDKWA (SEQ ID NO: 1) fusion-protein is $1.7 \times 10^7$ $M^{-1}$ [33] the inhibition pattern of Ab2 3H6 was acceptable for further studies.

Similar results were obtained when replacing GGGLELDKWASL (SEQ ID NO: 13) with other synthetic peptides containing the ELDKWA (SEQ ID NO: 1) epitope or slightly modified, particularly functionally equivalent, variants thereof including functionally equivalent homologues or functionally equivalent variants occurring due to the degeneracy of the genetic code and/or due to variability of the HIV-1 viruses, the variants preferably being selected from the group consisting of ELDNWA (SEQ ID NO. 2), ELNKWA (SEQ ID NO. 3), LELDKWA (SEQ ID NO. 4), LELDNWA (SEQ ID NO. 5), LELNKWA (SEQ ID NO. 6), ELDKWAS (SEQ ID NO. 7), ELDNWAS (SEQ ID NO. 8), ELKNWAS (SEQ ID NO. 9), LELDKWAS (SEQ ID NO. 10), LELDNWAS (SEQ ID NO. 11), LELNKWAS (SEQ ID NO. 12).

Virus Neutralization Assay with 3H6:

Interaction of 2F5 with the different Ab2s was further investigated in a neutralization assay as described previously [26]. The assay was performed with HIV-1 strain NL4-3 infected AA-2 cells (NIAID, Bethesda, Md.) as indicator cells using p24 antigen as virus replication marker. Serial dilutions of Ab2 antibodies (starting concentration of 250 µg/mL) were mixed with constant amounts of 2F5 or 2G12 as negative control (10 µg/mL of each neutralizing antibody) and pre-incubation with virus before addition of AA-2 cells and further incubated for 5 days. Virus replication was measured in a p24-ELISA at the time point of termination of the assay [34]. The ratios of p24 antigen production in Ab-containing cultures (Vn) to p24 antigen production in control cultures (Vo), taking into account the input p24, were calculated and Ab concentrations (µg/mL) causing x % neutralization were plotted. Each test included a virus titration to determine the actual tissue culture infectious dose 50 ($TCID_{50}$) and the viral titer was determined by linear regression analysis. Tests were considered to be valid in case of viral titers between $10^2$-$10^3$ $TCID_{50}$.

Figure 2:
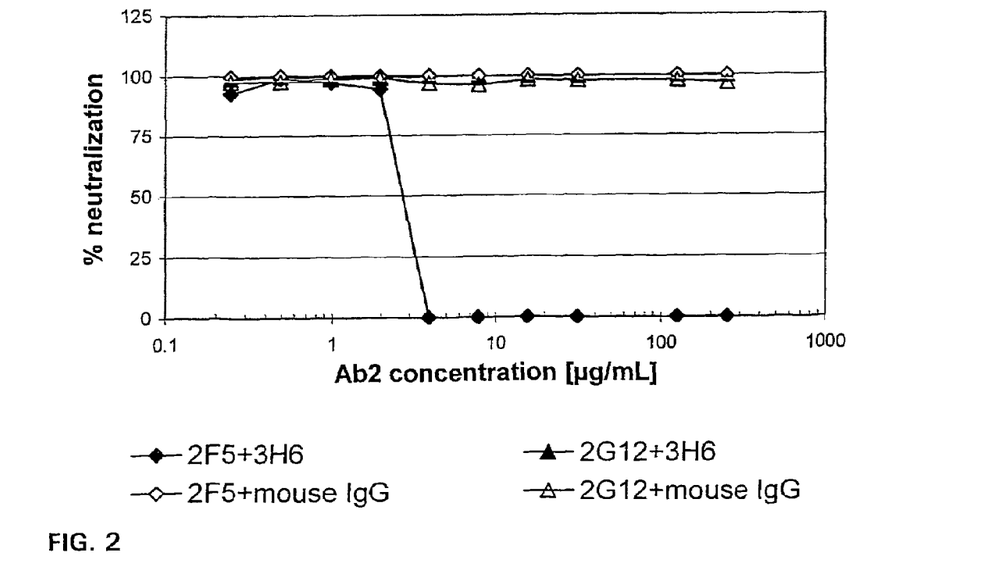
Figure 3:
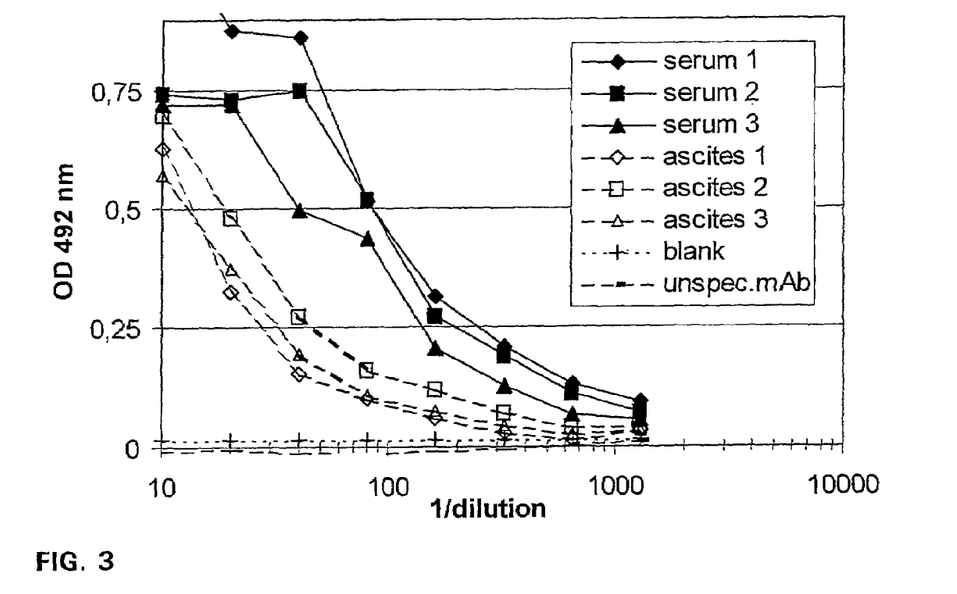
Figure 4:
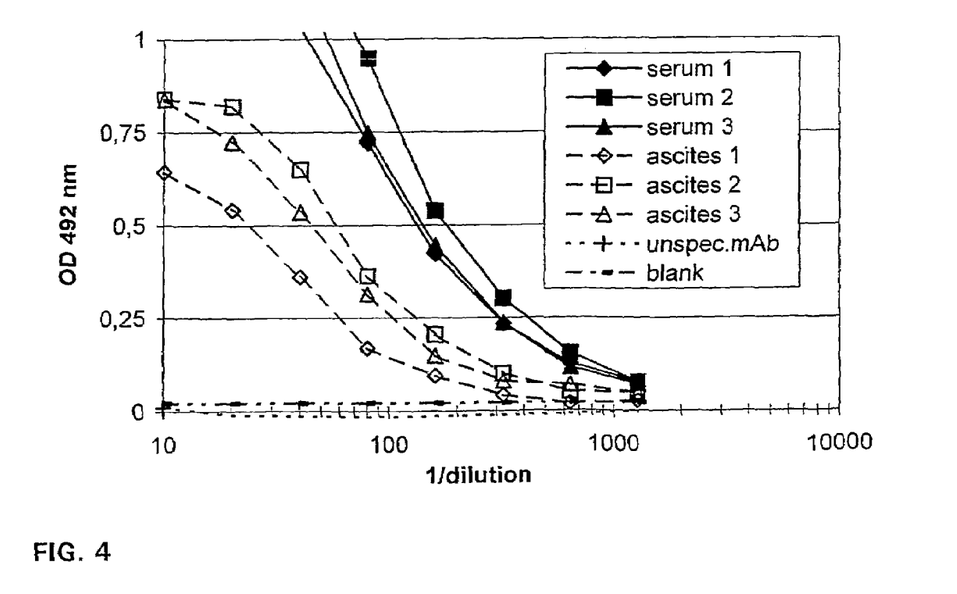
Figure 5:
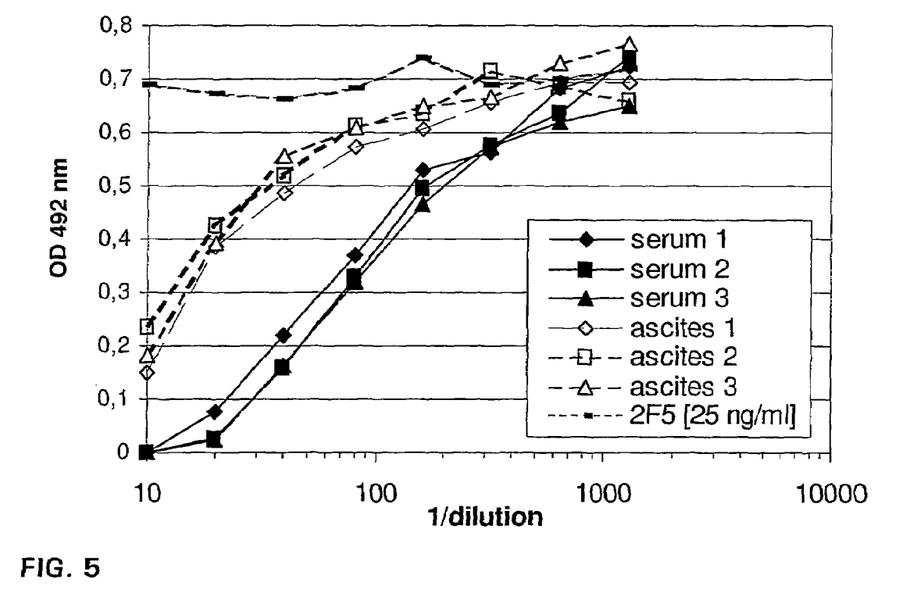

FIG. 2 shows the in vitro neutralization of HIV-1 NL4-3 after preincubation of Ab2 3H6 with 2F5 and 2G12. 2F5 and 2G12 alone neutralize 90% of the virus at a concentration of 3 µg/mL and 99% of the virus at 12 µg/mL and 11 µg/mL, respectively (data not shown). The 2F5 and 2G12 concentration was kept constant at 10 µg/mL. 50 µL of 2F5 or 2G12 were incubated with serial dilution of the Ab2s, 3H6, 4F6, 6F8 and only 3H6 was able to deplete neutralization of 2F5 (4F6 and 6F8 are not plotted). FIG. 1b describes the percent neutralization representing the remaining neutralizing capacity of 10 µg/mL 2F5 and 2G12 with increasing amounts of 3H6. 3.9 µg/mL of 3H6 extinguish the 2F5 neutralization properties and 1.9 µg/mL are able to reduce neutralizing capacity of 2F5 for 5%. This means that 3H6 and 2F5 react in nearly equimolar ratio, since the molecular weight of the two corresponding antibodies may vary due to oligomerization or cleavage. 3H6 is not able to reduce neutralization of 2G12 at concentration as high as 250 μg/mL. Ab2 3H6 was able to reduce 2F5 neutralization for 95% at 3.9 μg/mL.

Sequence of the variable regions of the heavy and light chains of antibody 3H6:

a) Amino acid sequence of the heavy chain variable region (vH) of anti-idiotypic antibody 3H6 (SEQ ID NO. 14):

GVQLQQSGPELVKTGASVKISCKASGYSFTDYFMHWVKQSHGKSLDWIGY

INCYTGATNYSQKFKGKATFTVDTSSNTAYMQFNSLTSEDSAVYYCARTS

IGYGSSPPFPYWGQGTLVTVSA b) Amino acid sequence of the light chain variable region (vL) of anti-idiotypic antibody 3H6 (SEQ ID NO. 15):

ETTVTQSPASLSMSIGEKVTIRCITSTDIDDDMNWYQQKPGEPPRLLISD

GNTLRPGVPSRFSSSGYGTDFVFTIENMLSEDVADYYCLQSDNLPYTFGG

GTNLEIK

EXAMPLE 3

Induction of Anti-Anti-Idiotypic Antibodies (Ab3)

Induction of Ab3 in BALB/c Mice:

After purification of Ab2 (3H6) by affinity chromatography it was digested with Mercuripapain (Sigma) and the digest purified with Protein-A-Sepharose 4 FF-column. Three BALB/c mice were injected with 5 μg of the 3H6Fab' intraperetoneally and after three weeks again, both times with Freund's incomplete adjuvant. Another week later the mice were sacrificed and blood and ascites samples were collected. The samples were analyzed by ELISA for IgG titer as described above.

Three BALB/c mice were immunized with 5 μg/mL 3H6Fab' fragment FIA solution. Unfortunately, after the second immunization the animals developed ascites and had to be sacrificed without finishing the immunization scheme. Serum and ascites were shown to have total IgG titers up to 2 mg/ml. The results of IgG titers, binding capacity and competition assay are summarized in Table 2. The binding to GGGLELDKWASL (SEQ. ID NO.13) and gp160 in an ELISA was illustrated in FIG. 2 by plotting the cut-off dilution of the polyclonal serum and ascites. End point titers (cut-off) were calculated as the reciprocal of the highest dilution that resulted in an OD at least two times greater than the OD obtained with corresponding preimmune IgG.

TABLE 2

| Sample | IgG titer [μg/mL] | Cut-off titer binding to gp 160 | Cut-off titer binding to ELDKWA (SEQ ID NO: 1) | 50% inhibition of 2F5/gp 160 binding | Neutralizing capacity ($IC_{50}$) |
|---|---|---|---|---|---|
| Serum 1 | 2271 | 1280 | 1280 | 1:60 | — |
| Serum 2 | 3776 | 1280 | 1280 | 1:120 | 1:14 |
| Serum 3 | 2603 | 1280 | 1280 | 1:120 | 1:12 |
| Ascites 1 | 1127 | 320 | 320 | 1:15 | — |
| Ascites 2 | 1958 | 640 | 640 | 1:15 | — |
| Ascites 3 | 1442 | 320 | 320 | 1:15 | — |

Characterization of Ab3:

Specificity of Ab3:

Serum and ascites samples of the 3H6 immunized mice were assayed for binding to the synthetic epitope GGGLELDKWASL (SEQ. ID NO.13) (1 μg/mL in coating buffer) and recombinant gp160 (1 μg/mL in coating buffer). The mouse antibodies were detected as described above. In another specificity test the serial dilutions of Ab3 samples were coincubated with a constant amount of 2F5 on a gp160 precoated plate. The 2F5 binding capacity at increasing dilutions of Ab3, starting with 1:10, was examined.

The 2F5 antibody was utilized at 25 ng/mL and a serial dilution of Ab3 samples starting with 1:10 was used as competitor. Ab3 sera that most potently competed with 2F5 binding on the antigen also exhibited in vitro neutralization potency. FIG. 3 illustrates the reduction of 2F5 binding to the precoated gp160 in terms of competition with the Ab3 samples.

Syncitium Inhibition Assay:

The neutralizing activity of Ab3 sera and ascites was assessed by inhibition of syncitium formation of HIV-1 strain $RF_{NT}$. Serial dilutions of serum, ascites or control antibody (2F5) were pre-incubated with virus ($10^2$-$10^3$ $TCID_{50}$/ml) for 1 h at 37° C. before addition of AA-2 cells. Starting dilutions of serum and ascites were 1:5 in culture medium. Cells were incubated for 5 days before assessment of syncitium formation. Experiments were performed with 4 replicates per dilution step. The presence of at least one syncitium per well was considered as indication for HIV-1 infection. The 50% inhibiting concentration ($IC_{50}$) was calculated according to the method of Reed and Muench [35]. Experiments included a virus titration of the inoculum to confirm the infectious titer.

The neutralizing properties of serum and ascites were tested with HIV-1 laboratory strain $RF_{NT}$. Samples were diluted initially 1:5, sterilized by 0.2µ filtration and used at a starting concentration of 1:10 in the AA-2 syncytia inhibition assay in quadruplicates. The virus-titer ($TCID_{50}$/ml) was determinated to be $10^{2.75}$. The ascites samples and serum 1 did not show any antiviral effect. Sera 2 and 3 reached an IC50 at dilutions 1:14.1 and 1:11.9 respectively. Serum 1 didn't show neutralization as well as the ascites samples.

EXAMPLE 4

Cytokine-Associated Antibody

3H6 vL and vH coding sequences are isolated from the murine mAb Ab2/3H6 via RT-PCR from the cultivated hybridoma cell line (see Example 1).

Thereafter human Cκ and IgG Fc domains are fused to the variable fragments of 3H6 by SOE-PCR (splicing by overlapping extension) and subsequently cloned into the eucaryotic expression vector pIRES. This cloning step results in a bicistronic expression cassette with CMV-promoter—chimeric 3H6 heavy chain-internal ribosomal entry site (IRES)—chimeric 3H6 light chain—SV40 polyA. The final plasmid is called p3H6 mhHC/LC.

Figure 6:
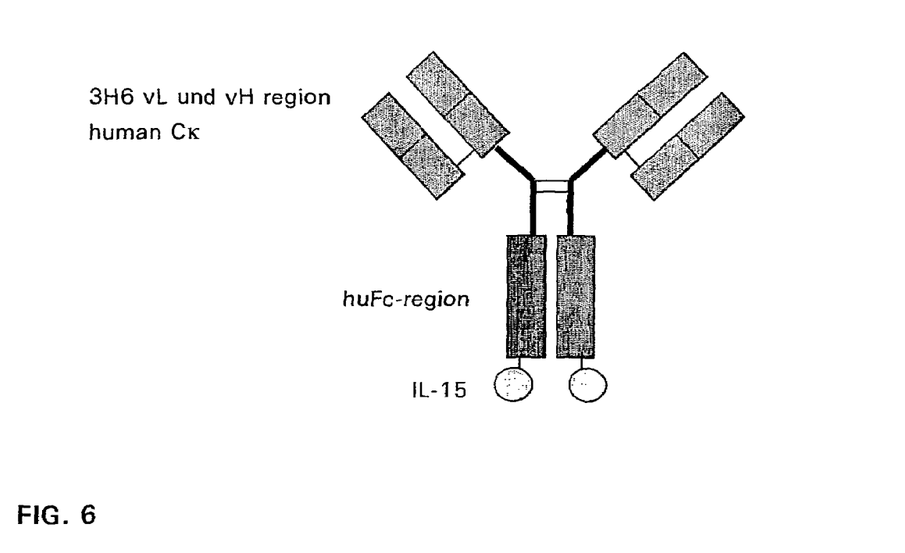

Human IL-15 cDNA is amplified by PCR and fused to the antibody heavy chain domain by SOE-PCR resulting in a fusion protein mo/hu3H6/IL-15 as shown in FIG. 6. This mo/hu3H6/IL-15 heavy chain replaces the 3H6 chimeric heavy chain in the expression plasmid p3H6 mhHC/LC resulting in the second expression plasmid p3H6 mhHC-IL-15/LC.

Two recombinant CHO-cell-lines are generated by cotransfection: one cell line expressing the mouse/human chimeric antibody mo/hu3H6 and the second cell-line expressing the same antibody with human IL-15 at the C-terminus of the 3H6 heavy chain (mo/hu3H6/IL-15).

The target plasmids described above are cotransfected together with the plasmid pdhfr coding for the mouse dihydrofolate-reductase (dhfr) by Lipofectin®. Subsequent selection of transfected cells is performed using geneticin sulfate (G418). Methotrexate (MTX) is used as amplification marker. After expansion of the subclones, screening for the best producing clone is done with an ELISA and flow cytometry with a commercial anti-human IL-15 mAb and the mAb 2F5. The selection process is repeated before the subclone with the highest secretion rate of the desired protein is expanded.

Thereafter, quantification and comparison of the amounts of secreted and intracellularly retained protein of the mo/hu3H6 or mo/hu3H6/IL-15 fusion protein is carried out.

Protein purification is done by affinity chromatography, optionally followed by ion-exchange chromatography. The isolated and purifed fusion protein mo/hu3H6/IL-15 is subjected to analytical determination of the biochemical properties including determination of:

affinity to the IL-2/IL-15-R using the Biacore or Isothermal Microcalorimetry;

molecule size using gel filtration columns and native gel electrophoresis;

in vitro stability of the immunocytokine by incubation in human serum;

competition assay of the mo/hu3H6/IL-15 fusion protein with the mo/hu3H6 antibody molecule to compare their binding capacity;

In vitro neutralisation experiments to describe the inhibiting properties of the mo/hu3H6 and the mo/hu3H6/IL-15 fusion proteins Diffusion through biological membranes, binding to the corresponding receptors, e.g. IL-2/IL-15-R on selected tissues using immuno-histological assays.

The construction and expression of the mo/hu3H6/IL-4 fusion protein is done analogously.

The results from in vitro experiments confirm both the HIV-1 neutralisation activity as well as the B cell response stimulating activity of the above disclosed fusion protein constructs of the present invention (data not shown herein).

REFERENCES

1. Herlyn, D., et al., *Anti-idiotype cancer vaccines: pre-clinical and clinical studies*. In Vivo, 1991. 5(6): p. 615-23.
2. Jerne, N. K., J. Roland, and P. A. Cazenave, *Recurrent idiotopes and internal images*. Embo Journal, 1982. 1(2): p. 243-7.
3. Nisonoff, A., *Idiotypes: concepts and applications*. Journal of Immunology, 1991. 147(8): p. 2429-38.
4. Ertl, H. C. and C. A. Bona, *Criteria to define anti-idiotypic antibodies carrying the internal image of an antigen*. Vaccine, 1988. 6(2): p. 80-4.
5. Bruck, C., et al., *Nucleic acid sequence of an internal image-bearing monoclonal anti-idiotype and its comparison to the sequence of the external antigen*. Proceedings of the National Academy of Sciences of the United States of America, 1986. 83(17): p. 6578-82.
6. Kennedy, R. C. and R. Attanasio, *Concepts of idiotype-based vaccines for hepatitis B virus and human immunodeficiency virus*. Canadian Journal Of Microbiology, 1990. 36(11): p. 811-6.
7. Hiernaux, J., C. Bona, and P. J. Baker, *Neonatal treatment with low doses of anti-idiotypic antibody leads to the expression of a silent clone*. Journal Of Experimental Medicine, 1981. 153(4): p. 1004-8.
8. Bhattacharya-Chatterjee, M. and K. A. Foon, *Anti-idiotype antibody vaccine therapies of cancer*. Cancer Treatment And Research, 1998. 94: p. 51-68.
9. Herlyn, D., et al., *Anti-idiotype vaccine in colorectal cancer patients*. Hybridoma, 1993. 12(5): p. 515-20.
10. Pohl, C., et al., *CD30-specific AB1-AB2-AB3 internal image antibody network: potential use as anti-idiotype vaccine against Hodgkin's lymphoma*. International Journal Of Cancer, 1993. 54(3): p. 418-25.
11. Rajadhyaksha, M., Y. F. Yang, and Y. M. Thanavala, *Immunological evaluation of three generations of anti-idiotype vaccine: study of B and T cell responses following priming with anti-idiotype, anti-idiotype peptide and its MAP structure*. Vaccine, 1995. 13(15): p. 1421-6.
12. Sikorska, H. M., *Therapeutic applications of antiidiotypic antibodies*. Journal Of Biological Response Modifiers, 1988. 7(4): p. 327-58.
13. Attanasio, R. and R. C. Kennedy, *Idiotypic cascades associated with the CD4-HIV gp120 interaction: principles for idiotype-based vaccines*. International Reviews Of Immunology, 1990. 7(1): p. 109-19.
14. Kang, C. Y., et al., *Development of HIV/AIDS vaccine using chimeric gag-env virus-like particles*. Biological Chemistry, 1999. 380(3): p. 353-64.
15. del Guercio, P., *AIDS and immune dysfunction. Alternative etiologic mechanisms*. Contributions To Microbiology And Immunology, 1989. 11: p. 289-304.

16. Sutor, G. C., et al., *Neutralization of HIV-1 by anti-idiotypes to monoclonal anti-CD4. Potential for idiotype immunization against HIV.* Journal Of Immunology, 1992. 149(4): p. 1452-61.
17. Shearer, M. H., et al., *Idiotype cascades associated with the CD4-HIV glycoprotein 120 interaction: immunization with anti-idiotypic antibodies induces anti-anti-idiotypic responses with anti-CD4 specificity and in vitro neutralizing activity.* Aids Research and Human Retroviruses, 2000. 16(1): p. 77-86.
18. Wilks, D., et al., *Antiidiotypic responses to immunization with anti-Leu 3a in human immunodeficiency virus-seropositive individuals.* Journal of Infectious Diseases, 1991. 163(2): p. 389-92.
19. Deckert, P. M., et al., *CD4-imitating human antibodies in HIV infection and anti-idiotypic vaccination.* Journal Of Immunology, 1996. 156(2): p. 826-33.
20. Boudet, F., J. Theze, and M. Zouali, *Anti-idiotypic antibodies to the third variable domain of gp120 induce an anti-HIV-1 antibody response in mice.* Virology, 1994. 200 (1): p. 176-88.
21. Fung, M. S., et al., *Monoclonal anti-idiotypic antibody mimicking the principal neutralization site in HIV-1 GP120 induces HIV-1 neutralizing antibodies in rabbits.* Journal Of Immunology, 1990. 145(7): p. 2199-206.
22. Connelly, R. J., et al., *Dual specificity of a monoclonal anti-idiotypic antibody for HIV-1 neutralizing monoclonals 110.3 and 110.4 as well as the V3 loop of gp120.* Virology, 1994. 205(2): p. 554-7.
23. Sperlagh, M., et al., *Polyclonal antiidiotypic antibodies mimicking gp120 of HIV-1.* Viral Immunology, 1994. 7(2): p. 61-9.
24. Ayyavoo, V., et al., *Immunogenicity of a novel DNA vaccine cassette expressing multiple human immunodeficiency virus (HIV-1) accessory genes.* Aids, 2000. 14(1): p. 1-9.
25. Ferko, B., et al, *Chimeric influenza virus replicating predominantly in the murine upper respiratory tract induces local immune responses against human immunodeficiency virus type 1 in the genital tract.* Journal of Infectious Diseases, 1998. 178(5): p. 1359-68.
26. Purtscher, M., et al., *A broadly neutralizing human monoclonal antibody against gp41 of human immunodeficiency virus type 1.* Aids Research and Human Retroviruses, 1994. 10(12): p. 1651-8.
27. Muster, T., et al., *A conserved neutralizing epitope on gp41 of human immunodeficiency virus type 1.* Journal Of Virology, 1993. 67(11): p. 6642-7.
28. Stoiber, H., et al., *Inhibition of HIV-1 infection in vitro by monoclonal antibodies to the complement receptor type 3 (CR3): an accessory role for CR3 during virus entry?* Molecular Immunology, 1997. 34(12-13): p. 855-63.
29. Stiegler, G., et al., *A potent cross-clade neutralizing human monoclonal antibody against a novel epitope on gp41 of Human Immunodeficiency Virus Type 1.* submitted, 2001.
30. Gorny, M. K. and S. Zolla_Pazner, *Recognition by human monoclonal antibodies of free and complexed peptides representing the prefusogenic and fusogenic forms of human immunodeficiency virus type 1 gp41.* Journal of Virology, 2000. 74(13): p. 6186-92.
31. Kunert, R., F. Rüker, and H. Katinger, *Molecular characterization of five neutralizing anti-HIV type 1 antibodies: identification of nonconventional D segments in the human monoclonal antibodies 2G12 and 2F5.* Aids Research And Human Retroviruses, 1998. 14(13): p. 1115-28.
32. Bruderer, U., et al., *Analyses of affinity distributions within polyclonal populations of antigen-specific antibodies. Evaluation of their accuracy in population detection using monoclonal antibodies.* Journal of Immunological Methods, 1992. 151(1-2): p. 157-64.
33. Kunert, R., et al., *Stable recombinant expression of the anti HIV-1 monoclonal antibody 2F5 after IgG3/IgG1 subclass switch in CHO-cells.* Biotechnology and Bioengineering, 2000. 67(1): p. 97-103.
34. Steindl,. F., et al., *A simple and robust method for the complete dissociation of HIV-1 p24 and other antigens from immune complexes in serum and plasma samples.* Journal of Immunological Methods, 1998. 217(1-2): p. 143-51.
35. Reed, L. J. and H. Muench, *A simple method of estimating fifty percent endpoints.* Am. J. Hygiene, 1938.27: p. 493-497.
36. Eckhart, L., et al., *Immunogenic presentation of a conserved gp41 epitope of human immunodeficiency virus type 1 on recombinant surface antigen of hepatitis B virus.* Journal of General Virology, 1996. 77 (Pt 9): p. 2001-8.
37. Hanson, L. A., et al., *Anti-idiotypic antibodies from the mother may influence the immune response of the fetus and newborn.* Acta Paediatrica Japonica, 1994. 36(2): p. 123-7.
38. Hanson, L. A., et al., *Immunoregulation mother-fetus/newborn, a role for anti-idiotypic antibodies.* Acta Paediatrica Scandinavica. Supplement, 1989.351: p. 38-41.
39. Forthal, D. N., et al., *Functional activities of 20 human immunodeficiency virus type 1 (HIV-1)-specific human monoclonal antibodies.* Aids Research and Human Retroviruses, 1995. 11(9): p. 1095-9.
40. Kozlowski, P. A., et al., *High prevalence of serum IgA HIV-1 infection-enhancing antibodies in HIV-infected persons. Masking by IgG.* Journal of Immunology, 1995. 154 (11): p. 6163-73.
41. Mascola, J. R., et al., *Summary report: workshop on the potential risks of antibody-dependent enhancement in human HIV vaccine trials.* Aids Research and Human Retroviruses, 1993. 9(12): p. 1175-84.
42. Szabo, J., et al., *Strong correlation between the complement-mediated antibody-dependent enhancement of HIV-1 infection and plasma viral load.* Aids, 1999. 13(14): p. 1841-9.
43. Fust, G., *Enhancing antibodies in HIV infection.* Parasitology, 1997. 115 Suppl: p. S127-40.

The invention claimed is:

1. A monoclonal antibody or fragment thereof which is reactive with HIV-1 neutralizing antibody 2F5 produced by a hybridoma cell line having the ECACC Accession No. 90091704 and which inhibits or prevents either or both of the HIV-1 neutralization activity of antibody 2F5 or the binding of antibody 2F5 to gp41 of I-IIV-1, the fragment being an antigen-binding part of the antibody which retains the binding specificity of the whole antibody, wherein the antibody is anti-idiotypic to antibody 2F5 and is produced by hybridoma cell line 3H6 having the ECACC Acc. No. 01100279.

2. The antibody or fragment thereof according to claim 1, wherein it inhibits or prevents binding of antibody 2F5 to proteins or peptides that comprise an amino acid sequence selected from the group consisting of SEQ ID NO. 1 to SEQ ID NO 12.

3. The antibody or fragment thereof according to claim 1, wherein it elicits upon administration to a mammal Ab3-type antibodies that have either or both of an HIV-1 neutralizing activity, or an ability to compete with antibody 2F5 for binding to proteins or peptides that comprise an amino acid sequence selected from the group consisting of SEQ ID NO. 1 SEQ ID NO 12.

4. The antibody or fragment thereof according to claim 1, wherein the antibody has either or both of a heavy chain variable region according to SEQ ID NO 14 or light chain variable region according to SEQ ID NO 15.

5. The antibody or fragment thereof according to claim 1, wherein the antibody is a chimeric mouse/human antibody or a humanized version of a mouse antibody.

6. The antibody or fragment thereof according to claim 1, wherein it is linked to an immunoactive molecule that increases or intensifies a B cell response.

7. A hybridoma cell line producing an antibody according to claim 1, the cell line being 3H6 deposited at PHLS, Porton Down, Salisbury, UK, under ECACC Acc. No. 01100279.

8. A composition comprising an antibody or antibody fragment defined in claim 1, and a pharmaceutically acceptable carrier.

9. The antibody or fragment thereof according to claim 6, wherein the immunoactive molecule is a cytokine selected from the group consisting of interleukin-4 (IL-4) and interleukin-1 5 (IL-15).

* * * * *